United States Patent
Maisel et al.

(10) Patent No.: US 10,646,434 B2
(45) Date of Patent: *May 12, 2020

(54) HYPOTONIC MICROBICIDAL FORMULATIONS AND METHODS OF USE

(71) Applicant: The Johns Hopkins University, Baltimore, MD (US)

(72) Inventors: Katharina Maisel, Troy, MI (US); Craig W. Hendrix, Ellicott City, MD (US); Laura Ensign, Towson, MD (US); Edward Fuchs, Westminster, MD (US); Richard Cone, Baltimore, MD (US); Justin Hanes, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 61 days.

This patent is subject to a terminal disclaimer.

(21) Appl. No.: 16/123,278

(22) Filed: Sep. 6, 2018

(65) Prior Publication Data

US 2019/0000750 A1 Jan. 3, 2019

Related U.S. Application Data

(63) Continuation of application No. 15/120,852, filed as application No. PCT/US2015/017120 on Feb. 23, 2015, now Pat. No. 10,092,509.

(60) Provisional application No. 61/943,421, filed on Feb. 23, 2014, provisional application No. 62/108,354, filed on Jan. 27, 2015.

(51) Int. Cl.
| | |
|---|---|
| *A61K 9/00* | (2006.01) |
| *A61K 8/90* | (2006.01) |
| *A61K 47/10* | (2017.01) |
| *A61K 9/51* | (2006.01) |
| *A61K 31/09* | (2006.01) |
| *A61K 31/365* | (2006.01) |
| *A61K 31/352* | (2006.01) |
| *A61K 9/06* | (2006.01) |
| *A61K 31/52* | (2006.01) |
| *A61K 31/675* | (2006.01) |

(52) U.S. Cl.
CPC ............ *A61K 9/0031* (2013.01); *A61K 8/90* (2013.01); *A61K 9/0034* (2013.01); *A61K 9/06* (2013.01); *A61K 9/5146* (2013.01); *A61K 9/5153* (2013.01); *A61K 31/09* (2013.01); *A61K 31/352* (2013.01); *A61K 31/365* (2013.01); *A61K 31/52* (2013.01); *A61K 31/675* (2013.01); *A61K 47/10* (2013.01)

(58) Field of Classification Search
None
See application file for complete search history.

(56) References Cited

U.S. PATENT DOCUMENTS

| | | |
|---|---|---|
| 4,997,652 A | 3/1991 | Wong |
| 5,034,506 A | 7/1991 | Summerton |
| 5,578,325 A | 11/1996 | Domb |
| 5,710,135 A | 1/1998 | Leenders |
| 5,869,130 A | 2/1999 | Ferrier |
| 5,932,462 A | 8/1999 | Harris |
| 6,007,845 A | 12/1999 | Domb |
| 6,287,588 B1 | 9/2001 | Shih |
| 6,413,539 B1 | 7/2002 | Shalaby |
| 6,495,164 B1 | 12/2002 | Ramstack |
| 6,509,323 B1 | 1/2003 | Davis |
| 6,589,549 B2 | 7/2003 | Shih |
| 6,706,289 B2 | 3/2004 | Lewis |
| 8,354,476 B2 | 1/2013 | Hanes |
| 8,409,607 B2 | 4/2013 | Hughes |
| 8,465,778 B2 | 6/2013 | Hughes |
| 8,481,069 B2 | 7/2013 | Hughes |
| 8,512,738 B2 | 8/2013 | Edelman |
| 8,628,801 B2 | 1/2014 | Garreta |
| 8,632,809 B2 | 1/2014 | Asgharian |
| 8,663,674 B2 | 3/2014 | Wen |
| 8,911,768 B2 | 12/2014 | Whitcup |
| 10,092,509 B2 * | 10/2018 | Maisel ............... A61K 31/52 |
| 2003/0068277 A1 | 4/2003 | Vanbever |
| 2004/0234611 A1 | 11/2004 | Ahlheim |
| 2005/0009910 A1 | 1/2005 | Hughes |
| 2007/0071756 A1 | 3/2007 | Peyman |

(Continued)

FOREIGN PATENT DOCUMENTS

| | | |
|---|---|---|
| WO | 9207866 | 5/1992 |
| WO | 2006063249 | 6/2006 |

(Continued)

OTHER PUBLICATIONS

Lisco, et al., Cell Host Microbe., 4:260. (Year: 2011).*
Ensign-Hodges, L., "Mucus-Penetrating Nanoparticles for Vaginal and Gastrointestinal Drug Delivery," dissertation, Johns Hopkins University. (Year: 2012).*
Date, et al., Antiviral Res., 96:430. (Year: 2012).*
Anton, et al. "Enhanced levels of functional HIV-1 co-receptors on human mucosal T cells demonstrated using intestinal biopsy", Aids, 14(2):1761-5 (2000).

(Continued)

*Primary Examiner* — Michael Barker
(74) *Attorney, Agent, or Firm* — Pabst Patent Group LLP

(57) ABSTRACT

Hypotonic microbicidal compositions including an antimicrobial, such as an antiviral compound, and a pharmaceutically acceptable carrier in a solution formulation having hypotonic osmolarity have been developed for administration rectally to the gastrointestinal mucosa. In a preferred embodiment for use in preventing or decreasing HIV infection, the microbicidal is tenofovir, or a prodrug or derivative thereof. The formulations may include additional agents such as surfactants to enhance cleansing, buffers, or preservatives. Polymers may be included for osmolarity as well as comfort.

16 Claims, 1 Drawing Sheet

(56) References Cited

U.S. PATENT DOCUMENTS

| | | | |
|---|---|---|---|
| 2007/0149593 | A1 | 6/2007 | Ghosh |
| 2007/0219122 | A1 | 9/2007 | Glazer |
| 2007/0231360 | A1 | 10/2007 | Peyman |
| 2008/0070920 | A1 | 3/2008 | Guo |
| 2008/0086199 | A1 | 4/2008 | Dave |
| 2008/0166411 | A1 | 7/2008 | Shah |
| 2008/0166414 | A1 | 7/2008 | Hanes |
| 2008/0305172 | A1 | 12/2008 | Ahlheim |
| 2009/0203709 | A1 | 8/2009 | Steinberg |
| 2010/0227905 | A1 | 9/2010 | Kabra |
| 2011/0262406 | A1 | 10/2011 | Campo |
| 2012/0052041 | A1 | 3/2012 | Basu |
| 2012/0157499 | A1 | 6/2012 | Hughes |
| 2012/0269894 | A1 | 10/2012 | Ahlheim |
| 2013/0071349 | A1 | 3/2013 | Robinson |
| 2013/0122064 | A1 | 5/2013 | Ahlheim |
| 2013/0316001 | A1 | 11/2013 | Popov |
| 2013/0316006 | A1 | 11/2013 | Popov |
| 2013/0316009 | A1 | 11/2013 | Popov |
| 2014/0031408 | A1 | 1/2014 | Edelman |
| 2014/0107025 | A1 | 4/2014 | Wirostko |
| 2014/0178475 | A1 | 6/2014 | Figueiredo |
| 2014/0248358 | A1 | 9/2014 | Figueiredo |
| 2014/0249158 | A1 | 9/2014 | Figueiredo |
| 2014/0276482 | A1 | 9/2014 | Astafieva |
| 2014/0294986 | A1 | 10/2014 | Liu |

FOREIGN PATENT DOCUMENTS

| | | |
|---|---|---|
| WO | 2007016380 | 2/2007 |
| WO | 2007084418 | 7/2007 |
| WO | 2010040188 | 4/2010 |
| WO | 2010132664 | 11/2010 |
| WO | 2013110028 | 7/2013 |
| WO | 2013166408 | 11/2013 |
| WO | 2013166436 | 11/2013 |
| WO | 2014047439 | 3/2014 |

OTHER PUBLICATIONS

Anton, et al., "First phase 1 double-blind, placebo-controlled randomized rectal microbicide trial using UC781 gel with a novel index of ex vivo efficacy", PloS one, 6(9):e23243 (2011).

Anton, et al., "RMP-02/MTN-006: a phase 1 rectal safety, acceptability, pharmacokinetic, and pharmacofynamic study of tenofovir 1% gel compared with oral tenofovir disproxil fumarate", Aids Res, 28(11):1412-21 (2012).

Astete and Sabliov, "Synthesis and characterization of PLGA nanoparticles", J Biomater Sci Polymer Ed., 17:247-89 (2006).

Bertschinger, et al., "Disassembly of polyethylenimine-DNA particles in vitro: implications for polyethylenimine-mediated DNA delivery", J Control Release, 116:96-104 (2006).

Cao, et al., "Quantification of the spatial distribution of rectally applied surrogates for microbicide and semen in colon with SPECT and magnetic resonance imagining", Br J Clin. Pharmacol, 74(6):1013-22 (2012).

Clark and Friend, "Pharmacokinetics and Topical Vaginal Effects of Two Tenofovir Gels in Rabbits", AIDS Res Hum Retroviruses, 28(11):1458-66 (2012).

Cu, et al., "In vivo distribution of surface-modified PLGA nanoparticles following intravaginal delivery", J Cont. Release, 156(2):257-64 (2011).

das Neves and Bahia, "Gels as vaginal drug delivery systems", Int J Pharm., 318(1-2):1-14 (2006).

Deosarkar, et al.., "Polymeric particles conjugated with a ligand to VCAM-1 exhibit selective, avid, and focal adhesion to sites of atherosclerosis" Biotech. Bioeng., 101(2):400-7 (2008).

Dezzutti, et al., "Reformulated tenofovir gel for use as a dural compartment microbicide" , J antimicrobial chemotherapythea, 67(9):2139-42 (2012).

Dong, et al., "Vascular cell-adhesion molecule-1 plays a central role in heproangiogenic effects of oxidative stress", PNAS, 108(35):14614-9 (2011).

Donnell, et al., "HIV protective efficacy and correlates of tenofovir blood concentrations in a clinical trial of PrEP for HIV prevention", J Aqune Defic Syndr., 66(3):340-8 (2014).

Dunmire and Katz, "Alteration of human sperm kinematics in cervical mucus due to nonoxynol-9", Contraception, 55:209-17 (1997).

Ensign, et al., "enhanced vaginal drug delivery through the use of hypotomic formulations that induce fluid uptake", Biomaterials, 34(28):6922-9 (2013).

Ensign, et al., "Mucus-penetrating nanoparticles for vaginal drug delivery protect against herpes simplex virus", Sci Transl Med., 4(138):138ra79 (2012).

Eyles, et al., "The transfer of polystyrene microspheres from the gastrointestinal tract to the circulation after oral administration in the rat", J Pharm. Pharmacol., 47:561-5 (1995).

Fuchs, et al., "Hyperosmolar sexual lubricant causes epithelial damage in the distal colon: potential implication for HIV transmission", J Infect Dis 195:703-710 (2007).

Fuchs, et al., "Quantitative assessment of altered rectal mucosal permeability due to rectally applied nonoxynol-9, biopsy, and simulated intercourse", J Infect Diseases, 207(9):1389-96 (2013).

Galea, et al., "Rectal douching and implications for rectal microbicides among populations vulnerable to HIV in South America: a qualitative study", Sexually Transmitted Infections, 90(1):33-5 (2014).

Gref, et al., "'Stealth' corona-core nanoparticles surface modified by polyethylene glycol (PEG): influences of the corona (PEG chain length and surface density) and of the core composition on phagocytic uptake and plasma protein adsorption", Colloids Surf Biointerfaces, 18:301-13 (2000).

Hendrix, et al., "MTN-001 randomized pharmacokinetic cross-over study comparing tenofovir vaginal-gel and oral tablets in vaginal tissue and other compartments", PloS one, 8(1):e55012 (2013).

Jain, "The manufacturing techniques of various drug loaded biodegradable poly (lactide-co-glycolide) (PLGA) devices", Biomaterials, 21(23):2475-90 (2000).

Lacey, et al., "Unacceptable side-effects associated with a hyperosmolar vaginal microbicide in a phase 1 trial", Int J STD AIDS, 21:714-7 (2007).

Lai, et al., "Mucus-penetrating nanoparticles for drug and gene delivery to mucosal tissues", Adv Drug Deliver Rev., 61:158-71 (2009).

Lai, et al., "Rapid transport of large polymeric nanoparticles in fresh undiluted human mucus", PNAS, 104:1482-7 (2007).

Lemoine, et al., "Mechanism of efficient transfection of the nasal airway epithelium by hypotonic shock", Gene Ther., 12(16):1275-85 (2005).

Lennemas, "Does fluid flow across the intestinal mucosa affect quantitative oral drug absorption? Is it time for a reevaluation?", Pharm Res., 12:1573-82 (1995).

Leyva, et al., "Isoosmolar enemas demonstrate preferential gastrointestinal distribution, safety, and acceptability compared with hyperosmolar and hypoosmolar enemas as a potential delivery vehicle for rectal microbicides", Aids Res., 29(11):1487-95 (2013).

Li, et al., "Microencapsulation by solvent evaporation: state of the art for process engineering approaches", Int. J. Pharm., 363(1-2):26-39 (2008).

Louissaint, et al., "Distribution of cell-free and cell-associated HIV surrogates in female genital tract after simulated vaginal intercourse", J Infect Diseases, 205(5):725-32 (2012).

Louissaint, et al., "Distribution of cell-free and cell-associated HIV surrogates in the colon after simulated receptive anal intercourse in men who have sex with men", Acquir Immune Defic Syndr., 59(1):10-17 (2012b).

Louissaint, et al., "Single dose pharmacokinetics of oral tenofovir plasma, peripheral blood mononuclear cells colonic tissue and virginal tissue", Aids Res., 29(11):1443-50 (2013).

Mayer, et al., "Safety and tolerability of tenofovir vaginal gel in abstinent and sexually active HIV-infected and uninfected women", Aids, 20(4):543-51 (2006).

(56) References Cited

OTHER PUBLICATIONS

McGowan, et al., "A phase 1 randomized double blind placebo controlled rectal safety and acceptability study of tenofovir 1% gel (MTN-007)", PloS one, 8(4):e60147 (2013).

McGowan, et al., Characterization of baseline intestinal mucosal indices of injury and inflammation in men for use in rectal microbicide trials (HIV prevention trials Network-056) Acquir Immune Defic Syndr., 46(4):417-25 (2007).

McGowan, et al., "Charm-01 a Phase 1 rectal safety acceptability PK/PD study of three tenofovir gels", 22nd conference on Retroviruses and opportunistic Infections. Seattle Washington (2015).

Meisel, et al. "Human rectal mucus: proctoscoppitc and morphological changes caused by laxatives", Gastroenterology, 72(6):1274-9 (1977).

Moench, et al., "Microbicide excipients can greatly increase susceptibility to genital herpes transmission in the mouse", BMC Infect Dis., 10:331 (2010).

Mundargi, et al., "Nano/micro technologies for delivering macromolecular therapeutics using poly(D,L-lactide-co-glycolide) and its derivatives", J. Control. Release, 125(3):193-209 (2008).

Nance, et al.,"A dense poly(ethylene glycol) coating improves penetration of large polymeric nanoparlicles within brain tissue", Sci Transl Med., 4(149):149ral119 (2012).

Noach, et al., "Effect of anisotonic conditions on the transport of hydrophilic model compounds across monolayers of human colonic cell lines", J Pharmacol Exp Ther., 270:1373-80 (1994).

Nuttail, et al., "Pharmacokinetics of tenofovir following intravaginal and intrarectal administration of tenofovir gel to rhesus macaques", Antimicrobial agents Chemo., 56(1):103-9 (2012).

Owen, et al., "Factors influencing nonoxynol-9 permeation and bioactivity in cervical mucus", J Control Release, 60:23-34 (1999).

Patterson, et al., "Penetration of tenofovir and emtricitabane in mucosal tissues: implication for prevention of HIV-I Transmission", Sci Transal Med.,3(112):112re4.

Phillips, et al., Lubricants containing N-9 may enhance rectal transmission o HIV and other STIs, Contraception, 70(2):107-10 (2004).

Pihl, et al., Comparative study of the effect of luminal hypotonicity on mucosal permeability in rat upper gastrointestinal tract\, Acta Physiol., 193:67-78 (2008).

Rajapaksa, et al., "Intranasal M cell uptake of nanoparticles is independently influenced by targeting ligands and buffer ionic strength", J Biol Chem., 285:23739-46 (2010).

Richardson-Harman, et al., Correlation between compartmental tenofovir concentrations and an Ex vivo rectal biopsy model of tissue inflexibility in the RMP-02/MTN-006 Phase I, PloS one, 9(10):e11507 (2014).

Rudolph, et al., "Aerosolized nanogram quantities of plasmid DNA mediate highly efficient gene delivery to mouse airway epithelium", Mol Ther., 12:493-501 (2005).

Sheng, et al., "In vitro macrophage uptake and in vivo biodistribution of PLA-PEG nanoparticles loaded with hemoglobin as blood substitutes: effect of PEG content", J Mater Sci Mater Med., 20(9):1881-91 (2009).

Sudol, et al., "Relative safety of sexual lubricants for rectal intercourse", Sexually trans diseases, 31(6):346-9 (2004).

Ventuneau, et al., "Acceptability of UC781 gel as a rectal microbicide among HIV-uninfected women and men", Aids Behav., 14(3):618-28 (2010).

Veronese, et al., "PEG-doxorubicin conjugates: influence of polymer structure on drug release, in vitro cytotoxicity, biodistribution, and antitumor activity", Bioconjig Chern.,16(4):775-84 (2005).

Wang, et al., "Addressing the PEG mucoadhesivity paradox to engineer nanoparticles that "slip" through the human mucus barrier", Angew Chem Int Ed Engl., 47:9726-9 (2008).

Wilson, et al., "Epithelial migration in the colon: filling in the gaps", Clin Sci., 93(2):97-108 (1997).

Yang, et al., "A multi-compartment single and multiple dose pharmacokinetic comparison of recently applied tenofovir 1% gel and oral tenofocir disoproxil fumarate". PloS one, 9(10:e106196 (2014).

Yokoyama, et al., "Characterization and anticancer activity of the micelle-forming polymeric anticancer drug adriamycin-conjugated polyethylene glycol)-poly(aspartic acid) block copolymer", Cancer Res., 50:1693-1700 (1990).

Zeitlin, et al., "Leakage of three commercial vaginal gels in women", Contraception, 68:139-55 (2003).

Zhang, et al., "ph-responsive nanoparticles releasing tenofovir intended for the prevention of HIV transmission", Eu J Pharma Biopharma., 79(3):526-36 (2011).

* cited by examiner

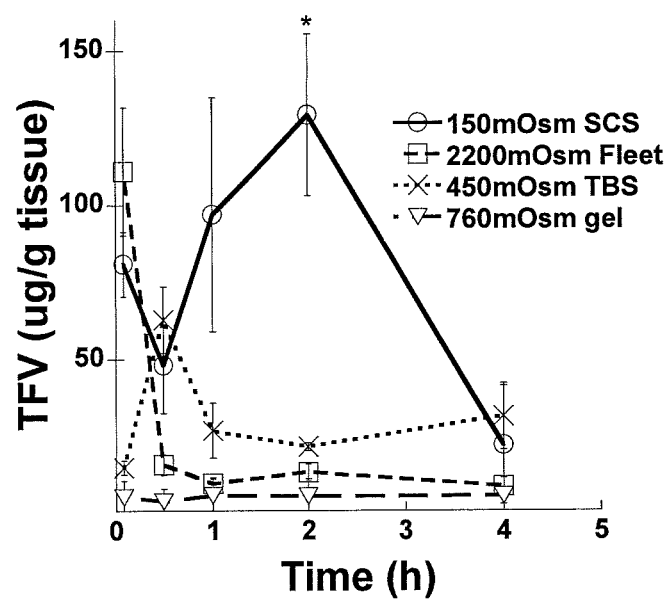

HYPOTONIC MICROBICIDAL FORMULATIONS AND METHODS OF USE

CROSS REFERENCE TO RELATED APPLICATIONS

This application is a continuation of U.S. application Ser. No. 15/120,852, filed Aug, 23, 2016, which is a National Phase application under U.S.C. § 371 of PCT/US2015/017120, filed Feb. 23, 2015 by Katharina Maisel, Craig W. Hendrix, Laura Ensign, Edward Fuchs, Richard Cone and Justin Hanes, entitled "Hypotonic Microbicidal Formulations and Methods of Use," which claims benefit of and priority to U.S. Ser. No. 61/943,421 filed Feb. 23, 2014 by Craig W. Hendrix, Justin Hanes, and Richard Cone for "Microbicidal Compositions and Methods of Use" and U.S. Ser. No. 62/108,354 filed Jan. 27, 2015 by Katharina Maisel, Laura Ensign, Justin Hanes, and Richard Cone for "Hypotonic Hydrogel Formulations for Enhanced Transport of Active Agents at Mucosal Surfaces", all of which are herein incorporated by reference in their entirety.

STATEMENT REGARDING FEDERALLY SPONSORED RESEARCH OR DEVELOPMENT

This invention was made with government support under Grant No. AI060614 awarded by the National Institutes of Health. The government has certain rights in the invention.

BACKGROUND OF THE INVENTION

UNAIDS estimates approximately 2.3 million new HIV infections in 2012, indicating an ongoing need for prevention of HIV infection. Men who have sex with men (MSM) are the group at highest risk of HIV acquisition through unprotected receptive anal intercourse (URAI) and are an important part of the epidemic in both developed and low and middle income countries. MSM remain the majority of the U.S. epidemic where most incident infections are among MSM (63% overall and 78% among men). These men also serve as a source of HIV infection for other risk groups. In Baltimore neighborhoods, 38% of MSM have HIV infection with seroincidence rates of 11% in young African American MSM. In a survey of U.S. MSM, 36% reported having RAI at last sex, and the percentage who reported not using condoms ranged from 38-65%. Women globally also engage in anal intercourse at 10-20% levels, substantial given their percent of the population, and report lower condom use than most MSM surveys. The combination of high RAI frequency, low condom use, and higher risk of HIV infection via RAI argues strongly for strategies to prevent HIV infection associated with URAI.

Pre-exposure prophylaxis (PrEP) with the NRTI tenofovir (TFV)-based drug regimens has been tested in 6 randomized controlled trials (RCTs) and demonstrates a clear plasma concentration-HIV protection response among studies. In iPrEx, the only study targeting MSM, daily oral TFV disoproxil fumarate (TDF)/emtricitabine (FTC) provided 92% protection with evidence of only 2 doses per week (measurable plasma TFV) whereas heterosexual studies indicated similar protection only with 6-7 doses per week.

Reports of enema use before sex by MSM range widely: 51-96% in New York City, 67% in Baltimore, 18-53% in African-Americans, and 28% in Peru. Typically, enemas were taken within 2 hours before and 1 hour after sex (when enemas are used less often) for reasons of hygiene, partner desire, and belief in HIV protection. Several MSM studies indicate between 80% and 100% willingness to use rectal microbicide enemas, especially in the absence of condoms.

A number of formulations have been tested for this purpose, for example, in prior IP/CP U19 programs, MDP (Anton, PI) and CHARM (McGowan, PI). For example, RMP-02/MTN-006 studied rectal application of VF (vaginal formulation) TFV 1% gel (used in CAPRISA 004 and VOICE), a very hyperosmolar formulation compared to RF (rectal optimized formulation, developed in MDP) and RGVF (reduced glycerin vaginal formulation, developed in MTN). RMP-02/MTN-006 demonstrated that VF applied rectally was associated with gastrointestinal-related Grade 3 adverse events (only during 7-day exposure) and less than desired acceptability. Another MDP study and a CDC funded study also demonstrated mucosal tissue abnormalities with hyperosmolar enemas and gels, respectively.

The rectal columnar epithelium is fragile and extremely vulnerable to HIV-1 infection, in part due to the proximity of sub-epithelial stromal tissues that are densely populated with cells receptive to incident HIV-1 infection, such as dendritic cells (DCs), macrophages and T-cells that express both CD4 and both HIV-1 co-receptors CCR5 and CXCR4. Although the mechanisms of viral uptake and infection across rectal mucosa are not fully established, such physiological and anatomical differences may explain why HIV is more readily transmitted across rectal than across the cervicovaginal genital epithelium. In conjunction with this higher transmission risk of rectal versus vaginal exposure to HIV, there is a higher concentration of tenofovir achievable in colonic tissue than in vaginal tissue. The plasma concentration of tenofovir associated with 90% protection (EC90) in PK/PD models, 107 ng/mL, was not achieved by the most highly adherent heterosexual subpopulations. Achievement of concentrations above 107 ng/mL requires fastidious adherence and daily dosing. This is in contrast to the protective effect for MSM which is achieved with only 2 to 4 doses of oral TFV per week.

Given the (1) very high efficacy of TFV-based PrEP, (2) more efficient delivery of active drug to the colon with rectal compared to oral dosing, (3) the large negative impact of poor adherence on PrEP outcomes, (4) frequency of URAI in men and women, and (5) the common pre-existing behavior of enemas use before and after RAI by many MSM, there exists an unmet need for the development of a pharmacokinetically-enhanced TFV prodrug enema capable of protecting subjects from HIV acquisition.

It is therefore an object of the present invention to provide formulations for administration rectally to deliver an effective amount of antimicrobial, especially antiviral, to reduce the likelihood of HIV infection.

It is a further object of the present invention to provide such formulations which are safe, comfortable and easy to store and use.

SUMMARY OF THE INVENTION

Hypotonic microbicidal compositions including an antimicrobial, such as an antiviral compound, and a pharmaceutically acceptable carrier in a solution formulation having hypotonic osmolarity have been developed for administration rectally to the gastrointestinal mucosa. In a preferred embodiment for use in preventing or decreasing HIV infection, the microbiocidal is tenofovir, or a prodrug or derivative thereof. The formulations may include additional agents such as surfactants to enhance cleansing, buffers, or preservatives. Polymers may be included for osmolarity as well as comfort.

The formulations are preferably stored at room temperature and administered rectally at least one hour before intercourse.

BRIEF DESCRIPTION OF THE DRAWINGS

FIG. 1 is a graph of the concentration of tenofovir in mouse colorectal tissue at up to 4 h after intrarectal administration in various vehicles. 1% tenofovir was administered in ultrapure water (20 mOsm), simulated colon solution (a fluid-based enema vehicle mimicking the ionic composition of feces, SCS) (150 mOsm), isotonic tris-buffered saline (TBS, 450 mOsm), gel containing 5% glycerol (760 mOsm), and FLEET® enema (2200 mOsm). Studies were performed in at least n=3 mice. Data are calculated as means±SEM. *$P<0.05$ using Student's t-test.

DETAILED DESCRIPTION OF THE INVENTION

I. Definitions

As generally used herein "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

"Biocompatible" and "biologically compatible", as used herein, generally refer to materials that are, along with any metabolites or degradation products thereof, generally non-toxic to the recipient, and do not cause any significant adverse effects to the recipient. Generally speaking, biocompatible materials are materials which do not elicit a significant inflammatory, immune or toxic response when administered to an individual.

The terms "gel" and "hydrogel", as used interchangeably herein, refer to a swollen, water-containing network of finely-dispersed polymer chains that are water-insoluble, where the polymeric molecules are in the external or dispersion phase and water (or an aqueous solution) forms the internal or dispersed phase. The chains can be chemically crosslinked (chemical gels) or physically crosslinked (physical gels). Chemical gels possess polymer chains that are connected through covalent bonds, whereas physical gels have polymer chains linked by non-covalent bonds or cohesion forces, such as Van der Waals interactions, ionic interaction, hydrogen bonding, or hydrophobic interaction.

The polymer chains are typically hydrophilic or contain hydrophilic polymer blocks. "Gel-forming polymers" is used to describe any biocompatible polymer, including homopolymers, copolymers, and combinations thereof, capable of forming a physical hydrogel in an aqueous medium when present at or above the critical gel concentration (CGC).

The "critical gel concentration", or "CGC", as used herein, refers to the minimum concentration of gel-forming polymer needed for gel formation, e.g. at which a solution-to-gel (sol-gel) transition occurs. The critical gel concentration can be dependent on a number of factors, including the specific polymer composition, molecular weight, temperature, and/or the presence of other polymers or excipients.

The term "thermosensitive gel-forming polymer" refers to a gel-forming polymer that exhibits one or more property changes with a change in the temperature. For example, some thermosensitive gel-forming polymers are water soluble below a certain temperature but become water insoluble as temperature is increased. The term "lower critical solution temperature (LCST)" refers to a temperature, below which a gel-forming polymer and solvent are completely miscible and form a single phase. For example, "the LCST of a polymer solution" means that the polymer is uniformly dispersed in a solution at that temperature (i.e., LCST) or lower, but aggregates and forms a second phase when the solution temperature is increased beyond the LCST.

"Hydrophilic," as used herein, refers to molecules which have a greater affinity for, and thus solubility in, water as compared to organic solvents. The hydrophilicity of a compound can be quantified by measuring its partition coefficient between water (or a buffered aqueous solution) and a water-immiscible organic solvent, such as octanol, ethyl acetate, methylene chloride, or methyl tert-butyl ether. If after equilibration a greater concentration of the compound is present in the water than in the organic solvent, then the compound is considered hydrophilic.

"Hydrophobic," as used herein, refers to molecules which have a greater affinity for, and thus solubility in, organic solvents as compared to water. The hydrophobicity of a compound can be quantified by measuring its partition coefficient between water (or a buffered aqueous solution) and a water-immiscible organic solvent, such as octanol, ethyl acetate, methylene chloride, or methyl tert-butyl ether. If after equilibration a greater concentration of the compound is present in the organic solvent than in the water, then the compound is considered hydrophobic.

As used herein, the term "treating" includes inhibiting, alleviating, preventing or eliminating one or more symptoms or side effects associated with the disease, condition, or disorder being treated.

The term "reduce", "inhibit", "alleviate" or "decrease" are used relative to a control. One of skill in the art would readily identify the appropriate control to use for each experiment. For example a decreased response in a subject or cell treated with a compound is compared to a response in subject or cell that is not treated with the compound.

As used herein the term "effective amount" or "therapeutically effective amount" means a dosage sufficient to treat, inhibit, or alleviate one or more symptoms of a disease state being treated or to otherwise provide a desired pharmacologic and/or physiologic effect. The precise dosage will vary according to a variety of factors such as subject-dependent variables (e.g., age, immune system health, etc.), the disease or disorder, and the treatment being administered. The effect of the effective amount can be relative to a control. Such controls are known in the art and discussed herein, and can be, for example the condition of the subject prior to or in the absence of administration of the drug, or drug combination, or in the case of drug combinations, the effect of the combination can be compared to the effect of administration of only one of the drugs.

"Excipient" is used herein to include any other compound that can be included in the formulation that is not a therapeutically or biologically active compound. As such, an excipient should be pharmaceutically or biologically acceptable and non-toxic to the subject when administered by the intended route.

The term "osmolarity", as generally used herein, refers to the total number of dissolved components per liter. Osmolarity is similar to molarity but includes the total number of moles of dissolved species in solution. An osmolarity of 1 Osm/L means there is 1 mole of dissolved components per L of solution. Some solutes, such as ionic solutes that dissociate in solution, will contribute more than 1 mole of dissolved components per mole of solute in the solution. For example, NaCl dissociates into Na$^+$ and Cl$^-$ in solution and thus provides 2 moles of dissolved components per 1 mole of dissolved NaCl in solution. Physiological osmolarity is typically in the range of about 280 to about 310 mOsm/L.

The term "tonicity", as generally used herein, refers to the osmotic pressure gradient resulting from the separation of two solutions by a semi-permeable membrane. In particular, tonicity is used to describe the osmotic pressure created across a cell membrane when a cell is exposed to an external solution. Solutes that readily cross the cellular membrane contribute minimally to the final osmotic pressure gradient. In contrast, those dissolved species that do not cross the cell membrane, "impermeable solutes", will contribute to osmotic pressure differences and thus tonicity. The term "hypertonic", as generally used herein, refers to a solution with a higher concentration of impermeable solutes than is present on the inside of the cell. When a cell is immersed into a hypertonic solution, water will flow out of the cell, concentrating the impermeable solutes inside the cell until it becomes equal to the concentration of impermeable solutes outside the cell. The term "hypotonic", as generally used herein, refers to a solution with a lower concentration of impermeable solutes than is present inside of the cell. When a cell is immersed into a hypotonic solution, water will flow into the cell, diluting the concentration of impermeable solutes inside the cell until it becomes equal to the concentration of impermeable solutes outside the cell. The term "isotonic", as generally used herein, refers to a solution wherein the osmotic pressure gradient across the cell membrane is essentially balanced and no water flows into or out of the cell. The same meanings for tonicity apply for water flow through intestinal epithelia; hypertonic solutions cause water to flow into the lumen, whereas hypotonic solutions cause water to flow out of the lumen. Tonicity depends on the permeability properties of the cell or epithelium to different solutes, whereas osmolarity depends only on the total concentration of all solutes.

The following abbreviations are used herein:
ddC zalcitabine
ddI didanosine
DLV delavirdine
DMPA depot medroxyprogesterone acetate
DP diphosphate
FDA Food and Drug Administration
FTC emtricitabine
HEC hydroxyethylcellulose
IDV indinavir
IL-2 interleukin-2
IND investigational new drug
In-DTPA $^{111}$Indium-DTPA
iPrEx Pre-Exposure Prophylaxis Initiative
IRB Institutional Review Board
IGF insulin-like growth factor
IUD intrauterine device
IV intravenous
MID median rectal infectious doses
mITT modified intent to treat analysis
MMC Mucosal Mononuclear Cells
MQAP-NICHD Microbicide Quality Assurance Program-National Institute of Child Health and Human Development
MSM Men who have Sex with Men
MTN Microbicide Trials Network
MTT [1-(4,5-dimethylthiazol-2-yl)-3,5-diphenylformazan]
N-9 Nonoxynol-9
NAAT Nucleic acid amplification test
NFV nelfinavir
NIAID National Institute of Allergy and Infectious Diseases
NICHD National Institute of Child Health and Human Development
NIH United States National Institutes of Health
NNRTI non-nucleoside reverse transcriptase inhibitor
NRTI nucleoside reverse transcriptase inhibitor
NVP nevirapine
PBMC Peripheral blood mononuclear cells
PCR Polymerase Chain Reaction
PD Pharmacodynamic(s)
PEP post-exposure prophylaxis
PK pharmacokinetic(s)
PMPA 9-[(R)-2-(phosphonomethoxy)propyl] adenine monohydrate
PSS polystyrene sulfonate
PRN As needed
QD Daily
RAI Receptive Anal Intercourse (refers to coitus only, does not include manual stimulation or the use of sex toys or purgatives)
RF Rectal formulation
RGVF reduced glycerin vaginal formulation
RM rectal microbicide
RMP Rectal Microbicide Program
RPR rapid plasma reagin
RT Reverse transcriptase
RTV ritonavir
SOP standard operating procedure
SQV saquinavir
SSP Study-specific procedures
SPECT/CT Single photon computed tomography/computed tomography
STD/STI Sexually Transmitted Disease/Infection
$^{99m}$Tc-DTPA Technetium-99m-DTPA
TAF tenofovir alafenamide fumarate (formerly GS7340)
TDF tenofovir disoproxil fumarate (oral tenofovir)
TFV tenofovir
TFV-DP tenofovir diphosphate
TER transepithelial resistance
ULN upper limit of normal
URAI Unprotected Receptive Anal Intercourse
UA urinalysis
UTI urinary tract infection
VF vaginal formulation
VI virus isolation
VM vaginal microbicide
ZDV zidovudine II. Compositions A. Hypotonic Carriers The compositions include a hypotonic carrier. The hypotonic carrier will typically be a biocompatible carrier that preferably causes little to no signs of irritation when administered to human subjects. The carrier can be naturally occurring or non-naturally occurring including both synthetic and semi-synthetic carriers. Preferred carriers are sodium-based. Other solutions, including sugar-based (e.g. glucose, mannitol) solutions and various buffers (phosphate-buffers, tris-buffers, HEPES), may also be used.

When hypotonic solutions are applied to an epithelial surface, water flows out of the lumen, into cells and across the epithelium. This can cause swelling of the epithelial cells. In some cases, when the osmotic pressure difference is too large, the epithelial cells may burst, causing tissue irritation or disruption of the epithelial lining.

Advective transport of solutes is dominated by the bulk flow of a fluid, as in a solution passing through a filter. Since the colon absorbs water to dry the feces, fluid absorption by the colorectum can transport drugs advectively to the epithelium with great rapidity, much faster than by diffusion, and can move solutes through the unstirred layer of mucus adhering to the colonic epithelium. This distributes solutes to the entire colorectal surface, and if the formulation composition selectively improves tissue absorption rather than systemic absorption, minimizes systemic toxic side effects. The formulation for drug delivery markedly improves the uniformity of distribution of drugs over the epithelial surface. The formulations are particularly effective for delivery of microbicides for preventing rectal HIV transmission, as well as therapeutic drugs for the colon.

An absorption-inducing (hypotonic) enema delivers drugs advectively to the colon epithelium by the bulk flow of water (advection) and is nontoxic. This was demonstrated by advective delivery of a small hydrophilic drug in solution (tenofovir, a candidate microbicide for blocking HIV). The absorption-inducing hypotonic enema formulations caused free drug to be transported rapidly to the epithelial surface, unimpeded by the unstirred mucus barrier coating the epithelium. Moreover, advective transport delivered free drug deep into the colorectal folds to reach virtually the entire colorectal epithelial surface. In contrast, secretion-inducing (hypertonic) enema formulations markedly reduced drug uptake, and caused free drug to be expelled from the colon. Enemas induced rapid absorption even when sodium chloride (NaCl) was moderately hyperosmolal with respect to blood (~500 vs ~300 mOsm), presumably because sodium is actively pumped out of the lumen of the colon.

Hypotonic solution refers to a solution that contains less impermeable solutes compared to the cytoplasm of the cell. Examples of hypotonic solutions include, but are not limited to, Tris[hydroxylmethyl]-aminomethane hydrochloride (Tris-HCl, 10-100 mM, pH. 6-8), (4-(2-hydroxyethyl)-1-piperazineethanesulfonic acid (HEPES, 10-100 mM, pH 6-8) and dilute solutions of PBS, such as a solution containing 0.2 grams KCl, 0.2 grams $KH_2PO_4$, 8 grams NaCl, and 2.16 grams $Na_2HPO_4*7H_2O$ in 1000 ml $H_2O$, and dilute solutions of normal saline (typically containing 0.9% NaCl).

The hypotonic carrier usually contains water as the major component. The hypotonic carrier can be water, although mixtures of water and a water-miscible organic solvent can also be used. Suitable water-miscible organic solvents include alcohols, such as ethanol, isopropanol; ketones, such as acetone; ethers, such as dioxane and esters such as ethyl acetate.

The hypotonic carrier can be water containing one or more tonicity modifying excipients. Sodium chloride is the excipient that is most frequently used to adjust tonicity of a solution. Other excipients used to adjust the tonicity of solutions include glucose, mannitol, glycerol, propylene glycol and sodium sulphate. Tonicity modifying excipients can include pharmaceutically acceptable salts such as sodium chloride, sodium sulfate, or potassium chloride. Other excipients used to adjust tonicity can include glucose, mannitol, glycerol, or propylene glycol.

The tonicity of a formulation varies for different cells and mucosal surfaces; it also depends on whether or not the cell or epithelium actively transports solutes and ions; e.g. it has been found that the isotonic point in the vagina for sodium-based solutions is about 300 mOsm/L, similar to the osmolarity of serum, but in the colorectum, it is significantly higher, about 450 mOsm/L (presumable because the colorectum actively transports sodium ions out of the lumen). In some embodiments the solution has a tonicity from 50 mOsm/L to 280 mOsm/L, from 100 mOsm/L to 280 mOsm/L, from 150 mOsm/L to 250 mOsm/L, from 200 mOsm/L to 250 mOsm/L, from 220 mOsm/L to 250 mOsm/L, from 220 mOsm/L to 260 mOsm/L, from 220 mOsm/L to 270 mOsm/L, or from 220 mOsm/L to 280 mOsm/L.

The hypotonic carrier can include one or more pharmaceutically acceptable acids, one or more pharmaceutically acceptable bases, or salts thereof. Pharmaceutically acceptable acids include hydrobromic, hydrochloric, and sulphuric acids, and organic acids, such as lactic acid, methanesulphonic acids, tartaric acids, and malcic acids. Pharmaceutically acceptable bases include alkali metal (e.g. sodium or potassium) and alkali earth metal (e.g. calcium or magnesium) hydroxides and organic bases such as pharmaceutically acceptable amines. The hypotonic carrier can include pharmaceutically acceptable buffers such as citrate buffers or phosphate buffers.

B. Hydrogel-Forming Polymers

Gel-forming compositions that are capable of forming uniform gel coatings on epithelial surfaces but do not gel under storage conditions can be used. The gel-forming compositions contain one or more gel-forming polymers in a hypotonic carrier, optionally containing one or more additional excipients and/or one or more therapeutic, prophylactic, or diagnostic agents.

Hypotonic carriers concentrate the gel-forming polymer at an epithelial surface, resulting in uniform gel formation on the surface.

Thermosensitive (aka thermoresponsive) hydrogels are solutions that undergo sol-gel transitions when 1) at or above the critical gelling concentration (CGC) and 2) at or above the critical gelling temperature. Thermosensitive gelling agents (at or above their CGC) used for biomedical applications are liquid at room temperature, but form gel at body temperature. The increase in temperature induces a rearrangement and alignment of the polymer chains, leading to gelation into a 3-dimensional structure. This phenomenon is generally governed by the ratio of hydrophilic to hydrophobic moieties on the polymer chain. A common characteristic is the presence of a hydrophobic methyl, ethyl, or propyl group. Any thermosensitive polymer that fits these criteria can be administered hypotonically below the CGC to mucosal epithelial and form a uniform gel coating in vivo. Any polymer that has thermosensitive gelling properties, with a critical gelling temperature at or below 37 C, can be used. Examples of thermosensitive gel formers that can be used include polyoxyethylene-polyoxypropylene-polyoxyethylene triblock copolymers such as, but not limited to, those designated by the CTFA names Poloxamer 407 (CAS 9003-11-6, molecular weight 9,840-14,600 g/mol; available from BASF as LUTROL® F127) and Poloxamer 188 (CAS 9003-11-6, molecular weight 7680-9510 g/mol; available from BASF as LUTROL® F68); TETRONICs tetra-functional block copolymers based on ethylene oxide and propylene oxide The hydrogels can be formed from individual gel formers or as a combination of gel formers. For example, a poloxamer and another gel former (e.g., a TETRONIC® polymer) may be used in combination to attain the desired characteristics. In addition, various forms of the same gel former (e.g., Poloxamer 188 and Poloxamer 407) can be combined to attain the desired characteristics.

The polymer is provided in a concentration less than the concentration that forms a gel in a test tube when heated to 37° C. The concentration must be sufficiently high, but below the CGC, such that water flow through the epithelium will concentrate the hydrogel to reach or exceed the CGC in vivo, so gelation will occur on the mucosal epithelial surface. The range of time that it takes for gelation to occur depends on the mucosal surface (the capacity and rate of water absorption), the tonicity of the solution administered (more hypotonic solutions will drive more rapid fluid absorption), and the concentration of polymer administered (if the polymer concentration is too low, not enough fluid absorption will occur to concentrate the polymer to its CGC). However, gelation generally occurs within 1 h in the vagina and colorectum.

C. Additional Agents

The hypotonic compositions can contain one or more agents to be delivered including therapeutic agents, prophylactic agents, diagnostic agents, and/or nutraceuticals. "Bioactive agent" and "active agent" are used interchangeably include without limitation physiologically or pharmacologically active substances that act locally or systemically in the body. A biologically active agent is a substance used for the treatment (e.g., therapeutic agent), prevention (e.g., prophylactic agent), diagnosis (e.g., diagnostic agent), cure or mitigation of disease or illness, a substance which affects the structure or function of the body, or pro-drugs, which become biologically active or more active after they have been placed in a predetermined physiological environment. Examples can include, but are not limited to, small-molecule drugs, peptides, proteins, antibodies, sugars, polysaccharides, nucleotides, oligonucleotides, aptamers, siRNA, nucleic acids, and combinations thereof. The agents can be a small molecule (e.g., molecular weight less than 2000, 1500, 1000, 750, or 500 atomic mass units (amu)) or a biomolecule, such as peptides, proteins, nucleic acids, polysaccharides, lipids, glycoproteins, lipoproteins, or combinations thereof. The agents can include one or more of those described in *Martindale: The Complete Drug Reference*, 37$^{th}$ Ed. (Pharmaceutical Press, London, 2011).

The formulations can contain a therapeutically effective amount of a therapeutic agent to treat, inhibit, or alleviate one or more symptoms of a disease state being treated or to prevent one or more symptoms of a disease or disorder. These formulations are intended to be used as antimicrobials, especially as antivirals, most especially as anti-HIV agents.

Exemplary classes of agents include, but are not limited to, synthetic and natural proteins (including enzymes, peptide-hormones, receptors, growth factors, antibodies, signaling molecules), and synthetic and natural nucleic acids (including RNA, DNA, anti-sense RNA, triplex DNA, inhibitory RNA (RNAi), and oligonucleotides), and biologically active portions thereof.

As used herein, the term "microbicide" or "microbicidal composition" means compounds that can be applied inside the rectum to protect against sexually transmitted infections (STIs) including HIV, especially when administered as microbicidal enema formulation suitable for rectal use.

As used herein, the term "Nucleoside and Nucleotide Reverse Transcriptase Inhibitors" or "NRTIs" include those compounds that exhibit anti-HIV effects by inhibiting the activity of HIV reverse transcriptase. In a preferred embodiment, the antiviral is a NRTI in a mildly hypotonic solution. Examples include, but are not limited to, abacavir (ABC), didanosine (ddI), emtricitabine (FTC), lamivudine (3TC), stavudine (d4T), tenofovir (TFV), zidovudine (AZT) and zalcitabine (ddC), and their physiologically functional derivatives. Examples of other classes of antiviral compounds include NNRTIs, protease inhibitors, fusion or entry inhibitors, and integrase inhibitors.

In the most preferred embodiment, the NRTI is tenofovir ((R)-9-(2-phosphonylmethoxypropyl)adenine; and phosphonic acid, [[(1R)-2-(6-amino-9H-purin-9-yl)-1-methylethoxy]methyl], which has the following structure:

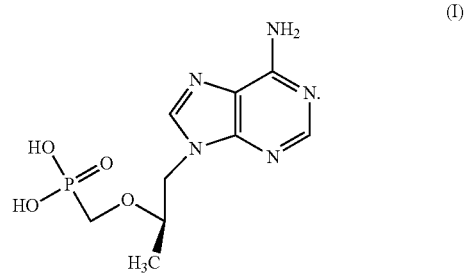 [SMILES: C[C@H](Cn1cnc2c(N)ncnc21)OCP(=O)(O)O]

In another embodiment, the NRTI used in the microbicidal formulations is tenofovir disoproxil fumarate (2,4,6,8-Tetraoxa-5-phosphanonanedioic acid, 5-[[(1R)-2-(6-amino-9H-purin-9-yl)-1-methylethoxy]methyl]-, bis(1-methylethyl) ester, 5-oxide, (2E)-2-butenedioate (1:1)) which has the following structure:

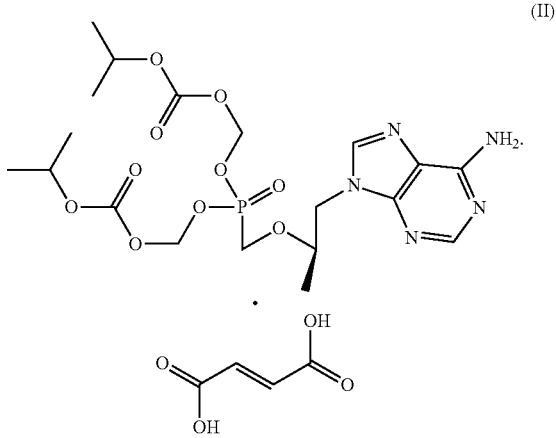

Examples of NNRTIs include, but are not limited to, for example, delavirdine, efavirenz, etravirine, rilpilvirine and nevirapine. Examples of protease inhibitors include, but are not limited to, for example, amprenavir, fosamprenavir, atazanavir, darunavir, indinavir, lopinavir, nelfinavir, ritonavir, saquinavir, and tipranavir. Examples of fusion or entry inhibitors include, but are not limited to, for example, enfuvirtide and maraviroc. Examples of integrase inhibitors include, but are not limited to raltegravir, elvitegravir, and dolutegravir.

Tautomeric forms, isomeric forms including diastereoisomers, and the pharmaceutically-acceptable salts thereof can also be used. The term "pharmaceutically acceptable salts" embraces salts commonly used to form alkali metal salts and to form addition salts of free acids or free bases. Examples of acids which may be employed to form pharmaceutically acceptable acid addition salts include such inorganic acids as hydrochloric acid, sulphuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. Suitable pharmaceutically acceptable salts include, for example, acid addition salts which may, for example, be formed by mixing a solution of the compound with a solution of a pharmaceutically acceptable acid, such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. All of these salts may be prepared by conventional means by reacting, for example, the appropriate acid or base with the corresponding compounds. Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, and procaine, or other pharmaceutically acceptable salts. Hydrates of the compounds may be used. The term "hydrate" includes but is not limited to hemihydrate, monohydrate, dihydrate, and trihydrate. Hydrates of the compounds may be prepared by contacting the compounds with water under suitable conditions to produce the hydrate of choice.

D. Proposed Formulations

The most commonly used commercial enema formulations rely on their hypertonicity to cause a large and rapid influx of water to cleanse the rectal vault. However, hypertonic sexual lubricant gels cause significant loss of single columnar epithelium within minutes of applying a single dose. In contrast, when an "isoosmolar" (osmolarity similar to that of blood) lubricant was used, there was no loss of single columnar epithelium. Other studies have also reported mucosal damage due to hypertonic solutions. A large proportion of users simply use tap water (a strongly hypotonic formulation) due to easy availability, however, epithelial loss (toxicity) has also been reported after its use. To address the potential use of an enema formulation of a microbicidal agent, either alone or as a complement to another method, a study was designed to assess the safety, distal gastrointestinal distribution, retention, and acceptability of three different types of enema. Given the concern for potential increased HIV acquisition posed by the widely used, strongly hypertonic enemas, a mild (hypotonicr/isoosmolar) enema was compared to the commonly used FLEET® (hypertonic) and distilled water (hypotonic) enemas in a cross-over design allowing paired comparisons within each individual.

As used herein, the terms "mildly hypotonic" or "near isotonic," means an aqueous solution or carrier having an osmolarity greater than tap water (0 mOsm), and between about 20 mOsm to about 290 mOsm. In some embodiments, the hypotonic or mildly hypotonic formulation of the microbicidal compositions have osmolarity in the range of 200 mOsm to about 240 mOsm, preferably about 220 mOsm. The microbicidal compositions are preferably formulated using known buffers and salts, including, for example, normal saline, phosphate buffered saline (PBS), Tris-buffered saline (TBS), or HEPES buffered saline.

As demonstrated by the examples, an enema formulation that has an osmolality of approximately 150 mOsm gave the best results. The solution contained both sodium (25 mM) and potassium (75 mM), but it was found that fluid absorption only occurred if sodium was present in the solution. If sodium was removed, leaving potassium unchanged at 75 mM (SCS-Na+), no fluid absorption occurred and TFV-FITC remained in the lumen. In contrast, if potassium was removed leaving sodium unchanged at 25 mM (SCS-K+), fluid was rapidly absorbed by the colorectal epithelium, distributing TFV throughout all of the folds of the mouse colorectum.

III. Methods of Administration

The formulations described herein are prepared and administered as described in the examples. Typically, the formulations are prepared as pre-solublized drug which is in a single use, squeezable container with a flexible tip for ease of rectal insertion prior to anal intercourse. The formulation could also be administered at the time of or immediately after intercourse, although this is not preferred.

The formulations may also be provided as a tablet which is added to a reusable or single use container, to which deionized water is also added to dissolve the tablet. The tablet contains salts, gel forming polymer as well as the microbiocide and any other additives.

For rectal administration, it may be preferred to use an applicator which distributes the composition substantially evenly throughout the rectum. For example, a suitable applicator is a tube 2.5 to 25 cm, preferably 5 to 10 cm, in length having holes distributed regularly along its length which is capable of distribution of the formulations within the colon.

The terms "reduce", "suppress" and "inhibit," as well as words stemming therefrom, have their commonly understood meaning of lessening or decreasing. These words do not necessarily imply 100% or complete treatment, reduction, suppression, or inhibition.

In some embodiments, the microbicidal compositions are administered to the rectum of the subject at least 30 minutes to 3 hours before RAI. In other embodiments, the microbicidal compositions are administered to the rectum of the subject at least 30 minutes to 2 hours after RAI. The formulations may provide inhibition of HIV infection of the colon and rectum for up to 7 days post application with one or doses.

Patterns of use of enemas underline the importance of the rapid achievement of sustained drug levels in the relevant tissues. Modeling studies indicate oral TFV PrEP regimens require one week to achieve protective concentrations of the active drug form, TFV diphosphate (TFV-DP), in tissue. These concentrations can be achieved within 30 minutes after TFV 1% rectal gel dosing. Another marked advantage of topical strategies is the limited systemic absorption of drug, which minimizes adverse long- and short-term systemic side effects.

The present invention will be further understood by reference to the following non-limiting examples.

EXAMPLE 1

Effect of Osmolality of Sodium Based Solutions on Colorectal Drug Distribution

Materials and Methods
Animal Model

Rodents are commonly used as animal models for delivery to the gastrointestinal tract. However, their defecation rate is much more rapid than typical for humans, and their hard, desiccated pellets do not resemble human feces. To simulate the softer stool consistency and less frequent defecation rate of humans, female 6-8 week old CF-1 mice (Harlan) were starved for 24 h to make the feces softer, more human-like, and less abundant. Mice were housed in cages with wire bottoms to prevent coprophagia. 20 or 50 µl of the various test solutions were administered to mice intrarectally with a Wiretrol (Drummond, Inc.). Control experiments confirmed that the osmolality of vehicles administered after DI water cleansing enemas was unaltered when vehicle fluid was collected after expulsion, indicating that this cleansing enema did not affect fluid absorption. Mice were anesthetized with the drop-method via isofluorane for shorter times, or injected with 300 mg/kg avertin (2, 2, 2-Tribromoethanol), using a 20 mg/mL working solution in phosphate buffered saline (PBS), when more extended anesthesia times were required. All experimental procedures were approved by the Johns Hopkins Animal Care and Use Committee.

Enema Formulations

10× Tris-buffered saline (Mediatech; 1×TBS is 20 mM Tris, 138 mM NaCl, pH 7.4) was diluted with ultrapure water to obtain sodium-based solutions of various osmolalities. Similarly, potassium phosphate buffer was prepared by dilution of 1 M $K_2HPO_4$ (Sigma) pH 5.5, with ultrapure water to obtain potassium-based solutions of various osmolality (e.g. 150 mOsm buffer was made by diluting 1M $K_2HPO4$ approximately 12 fold). The simulated colon solution (SCS) was made by dissolving sodium bicarbonate, potassium chloride, dibasic potassium phosphate and monobasic potassium phosphate (Sigma) in ultrapure water at the following ion concentrations: 75 mM K, 25 mM Na, 35 mM Cl, 30 mM $PO_4$, and 25 mM $CO_3$. Solution osmolality was measured with a vapor pressure osmometer (Wescor Vapro). FLEET® enema solution and FLEET® Naturals were purchased over the counter, and all enema solutions were sterile-filtered through a 0.2 μm filter prior to in vivo use. A 5% w/v glycerol gel was obtained by mixing the universal placebo HEC gel (ReProtect, Inc.) with glycerol.

Toxicity of Enema Formulations in the Mouse Colorectum

Mice were anesthetized by avertin, and 50 μl of tap water, SCS, or FLEET® was administered. Mice were kept in supine position for 20-30 min prior to sacrificing them and excising the tissues. Tissues were fixed in formalin and taken to the Johns Hopkins Medical Institutions Reference Histology Laboratory for standard paraffin embedding, sectioning, and hematoxylin and eosin (H&E) staining. Images were obtained using a light microscope with a 10×/0.25 NA objective (Nikon E600).

Free Drug Uptake into Plasma after Administration to the Mouse Colorectum

Mice were anesthetized using avertin, and 20 μl of the various solutions containing 1% w/v unlabeled TFV and 1 μL of $H^3$-TFV (1 mCi/ml, suspended in ethanol, Moravek Biochemicals) was administered intrarectally. For the 0 min time point, retro-orbital blood collection was used to collect blood immediately after administration of each solution; for the 30 min time point blood was removed 30 min post administration. Whole blood was centrifuged in heparinized tubes to obtain plasma, and 200 μl of plasma was dissolved in 5 ml of SOLVABLE™ and bleached using hydrogen peroxide. 500 μl of plasma/SOLVABLE™ solution was added to 10 ml of Ultima Gold and $H^3$ content was analyzed using a scintillation counter. Concentrations were calculated using a calibration curve of free $H^3$-TFV. A serial dilution of $H^3$-TFV was made to include the full range of sensitivity of the scintillation counter. Separate standard curves were made for lower and higher count samples. Concentrations of $H^3$-TFV in plasma were estimated using the standard curves. $H^3$-TFV was administered in a 1% unlabeled TFV solution to ensure no difference in uptake because of drug concentrations. Total drug concentration in plasma was calculated assuming that radioactively labeled and unlabeled drugs were taken up at similar rates.

Pharmacokinetic Studies of Free Drug in the Mouse Colorectal Tissue

Mice were anesthetized using avertin, and 20 μl of the various solutions containing 1% (w/v) unlabeled TFV and 1 μl $H^3$-TFV (1 μCi/mouse) was administered intrarectally to mice. Tissue was harvested at 5 min, 30 min, 1 h, 2 h, and 4 h time points and processed as described above. $H^3$ tissue content was measured using a scintillation counter and normalized based on individual tissue weights. Values were obtained from n=5 mice, and the highest and lowest values were removed from each group to obtain n=3 per time point for each solution used.

Results

Studies in the mouse vagina showed that vehicles causing advective absorption (hypotonic) are advantageous for improving the distribution of water soluble hydrophilic drugs at mucosal surfaces. Studies were performed to demonstrate colorectal delivery of TFV in a hypotonic enema vehicle for HIV pre-exposure prophylaxis (PrEP). TFV was covalently labelled with FITC (TFV-FITC) and mixed at a 1:10 ratio with unlabeled TFV to visualize distribution. Sodium-based enema vehicles of varying osmolality were compared: deionized water and isotonic saline (300 mOsm), which induce absorption, an essentially isotonic TBS (450 mOsm), and a slightly hypertonic TBS (650 mOsm) that induces fluid secretion.

FIG. 1 is a graph of the concentration of tenofovir in mouse colorectal tissue at up to 4 h after intrarectal administration in various vehicles. 1% tenofovir was administered in ultrapure water (20 mOsm), simulated colon solution (a fluid-based enema vehicle mimicking the ionic composition of feces, SCS) (150 mOsm), isotonic tris-buffered saline (TBS, 450 mOsm), gel containing 5% glycerol (760 mOsm), and FLEET® enema (2200 mOsm). The graph shows significantly higher levels of TFV with the 150 mOsm formulation.

Distribution in transverse colonic cryosections after rectal administration of 1% TFV-FITC in TBS vehicle (450 and 650 mOsm), DI water (20 mOsm), and isoosmolar saline (310 mOsm) showed that colorectal tissue coverage (and therefore access to target cells and tissues) was improved by using an absorption inducing enema. Bulk fluid flow transports the water-soluble, small molecule drug through the mucus barrier and into the epithelium, and also transports the drug deep into the folds of the (collapsed) colorectum.

To minimize risk of epithelial toxicity that could be caused by osmotic gradients much larger than typically occur in the colon, an enema formulation that has sodium and potassium concentrations similar to those found in feces was used. The osmolality of the simulated colon solution (SCS) was approximately 150 mOsm. Since the solution contained both sodium (25 mM) and potassium (75 mM), the effect of the individual contributions of these ions were assessed. It was found that fluid absorption only occurred if sodium was present in the solution. If sodium was removed, leaving potassium unchanged at 75 mM (SCS-Na+), no fluid absorption occurred and TFV-FITC remained in the lumen. In contrast, if potassium was removed leaving sodium unchanged at 25 mM (SCS-K+), fluid was rapidly absorbed by the colorectal epithelium, distributing TFV throughout all of the folds of the mouse colorectum.

Toxicity of Enema Formulations

Hyper-osmolar (and hyper-tonic) enema solutions are toxic to the human colorectal epithelium. Acute tissue effects were investigated to ensure that hypotonic enema formulations would be safer to use in the colorectum. Two frequently used enema formulations, tap water and FLEET®, as well as the SCS formulation in the mouse colorectum. The FLEET® enema caused distension and epithelial disruption within 10 min of administration. In contrast, SCS and tap water enemas did not induce detectable epithelial effects compared to control tissues.

Effect of Tonicity on Colorectal Drug Uptake into Plasma and Tissue

Very hypotonic delivery of free drug causes decreased vaginal retention, likely due to the drug being driven advectively all the way through the epithelium to reach systemic circulation. These studies investigated the effect of enema tonicity on movement of drugs from the colorectal lumen into the plasma. Drug delivered in a variety of solutions including tap water, the optimized enema formulation (SCS) that causes only mild advective absorption, iso-osmolal 0.9% saline (often mis-termed "isotonic"), FLEET® enema and a mild secretion-inducing (hypertonic) solution containing 5% glycerol in DI water were compared.

No TFV was detected in the plasma after 30 minutes if administered in isotonic and mildly hypotonic solutions (SCS); however, TFV could be found in the plasma 30 min after enema administration in very hypotonic (DI water) and very hypertonic solution (FLEET®). These results indicate that TFV delivery to the colo-rectal tissue was optimally achieved with mildly hypotonic solutions.

The amount of TFV associated with colorectal epithelial tissue was compared when administered in the same set of solutions. Based on cell migration data and the number of cell layers these cells need to ascend through the crypts in the mouse colorectum, it was calculated that the surface epithelial layer, which would absorb drug, renews approximately every 2 h (Chang 1975, Chang 1971). Accordingly, tissue concentration was assessed up to 4 h, at which time tissue concentrations became low and indistinguishable between the different solutions. The initial tissue TFV concentrations were highest when administered in FLEET® and in SCS compared to administration in isotonic solution. At 2 hours, tissue concentrations of TFV administrated in FLEET® or isotonic TBS were significantly lower than when administered in SCS. The area under the curve (AUC) for SCS, isotonic 450 mOsm TBS, FLEET® enema, and 5% glycerol gel were 330, 120, 72, and 21 µg·h/g, respectively. Even though the 5% glycerol gel was only moderately hypertonic, it decreased TFV in the tissue by more than 10-fold. This indicates that free drug is best administered in a mildly absorption-inducing solution to maximize drug retention within the tissue compared to both isotonic (non-absorbing) and hypertonic (secretion inducing) solutions.

TFV, delivered as free drug in mildly hypotonic sodium-based solutions, caused rapid, well-distributed, and prolonged colorectal tissue uptake of TFV in mice with no detectable systemic absorption. In mouse studies, mildly hypotonic SCS provides increased colorectal tissue drug levels compared to isotonic TBS and mildly hypertonic gel containing 5% glycerol. Furthermore, the strongly hypertonic FLEET® enema caused very rapid osmotically-driven flux of water into the lumen, triggering expulsion that limited colorectal distribution. PK benefits of hypotonic delivery in mice cannot be tested beyond 2 h, as epithelial cell turnover in the mouse colorectum occurs approximately every 2 hours.

EXAMPLE 2

Clinical Studies Comparing Efficacies of Different Osmolarity Formulations

Materials and Methods

The osmolarity study of the formulation for use with the microbicide and informed consent document was approved by the Johns Hopkins Institutional Review Board. The study was a randomized, blinded comparison of distribution, toxicity and acceptability of three different types of enema (rectal douche) of varying osmolarity in healthy MSM. The hyper-osmolar, hypo-osmolar, and mild hypo-osmolar/iso-osmolar enemas consisted of a commercial FLEET® Phosphate Enema of approximately 2,200 mOsmols/kg (Fleet Laboratories, Lynchburg, Va.), 125 ml distilled water (0 mOsmols/kg), and 125 ml NORMOSOL®-R enema (294 mOsmols/kg) with pH 7.4 (Hospira, Inc., Lake Forest, Ill.), respectively; all were administered via an enema bottle.

Study Subjects Nine HIV negative healthy male research participants without history of anorectal disease participated in the study. Each research participant provided written informed consent followed by eligibility screening which included medical history, physical examination, and laboratory tests. Eligible research participants received each enema formulation four separate times with a washout period of two weeks between formulations. Before receiving the first enema, all subjects had a baseline sigmoidoscopy study at least two weeks before the first formulation. The first dose was administered in an inpatient setting followed by detailed analysis of distribution and toxicity via SPECT/CT imaging and histology of colon biopsies. Three more doses were self-administered by the research participants in outpatient settings in the context of RAI. Inpatient enemas contained a radioactive small molecule to simulate added microbicide, and enabled measurement of colon distribution using SPECT/CT and changes in rectal mucosal permeability by measuring radiolabel in blood. Toxicity was assessed by quantifying tissue damage in colonic biopsies collected after dosing. Acceptability was assessed using a series of web-based questionnaires and a structured interview at the end of the study. All research participants and all study personnel were blinded to enema product type which was dispensed by the unblinded investigational research pharmacist according to a randomization sequence.

Dose Preparation and Administration. Inpatient doses were prepared by mixing 1 mCi 99mTc-DTPA (Cardinal Health, Halethorpe, Md.) with 125 ml test enema and administered to research participants. For outpatient dosing, the volunteers were provided with 3 individual doses of each enema type without radiolabel following hospital discharge. Volunteers self-administered these doses in the context of RAI during periods ranging from weeks to several months until completion.

Sigmoidoscopy and Biopsy Collection. Sigmoidoscopy by a gastroenterologist blinded to treatment assignment was performed approximately 1 hour after the first dose of each of the three study products. The procedure was performed using a flexible sigmoidoscope (Evis Exera, Olympus America Corp., Center Valley, Pa.) with the subject in the left lateral decubitus position. Once the sigmoidoscope was inserted, 3.3 mm pinch-biopsy forceps (Microvasive n°. 1599; Boston Scientific Corp., Natick, Mass.) were introduced through the sigmoidoscope and biopsies were acquired separately at 5, 10, and 20 cm distance from the anus following this same sequence to prevent contamination due to scope movement. Each biopsy was placed in tissue culture RPMI 1640 medium containing L-Glutamine, 25 mM HEPES (Mediatech, Herndon, Va.) pen/strep antibiotic and 10% fetal bovine serum (Invitrogen, Carlsbad, Calif.). Endoscopic brushes (Cytobrush model n°. 60315; Ballard Medical Products, Draper, Utah) were used separately to collect sample from the mucosal surface. Two biopsies and three brushes were taken at each designated location. From prior studies, it was determined that proximal distribution of rectally applied radiotracer is typically beyond the 20 cm distance, so sigmoidoscopy was not believed to alter the upper extent of enema distribution 24. Biopsies were fixed in formalin in preparation for histological examination.

Mucosal Interferon-Gamma. Levels of IFN-gamma (IFN-γ) mRNA from colonic brush samples were measured using qPCR as described J. Am. Statistical Assn., 2008; 103(484): 1470-1480. Standardization across samples was achieved by expressing cytokine copy number per 106 beta-actin copies per sample. All assays were performed in triplicate and reported as mean from the 3 measurements.

SPECT/CT Imaging Distribution. After sigmoidoscopy at 2, 4 and 24 hours after dosing, SPECT/CT imaging was performed to assess colonic distribution of the radiolabel. Participants were imaged using a dual-head VG SPECT/CT series system (GE Medical Systems, Waukesha, Wis.) equipped with a CT (computed tomography) unit (Hawkeye). In brief, CT images were acquired before SPECT acquisition for anatomical reference and to generate an attenuation correction map for SPECT image reconstruction. CT images were reconstructed with a filtered back projection algorithm onto a 256×256-matrix size. After SPECT acquisition, images were reconstructed using the OSEM algorithm and fused using the General Electric eNTEGRA workstation, software version 1.04 (GE Medical Systems, Waukesha, Wis.) into a 128×128×128 matrix size with each voxel representing 3.45 $mm^3$. In images showing activity in the bladder or on the perianal or intergluteal skin, the signal was subtracted using in-house software.

Curve-fitting and concentration-by-distance calculations were done using R version 2.13.1 (The R Foundation for Statistical Computing, Vienna, Austria) according to previously described algorithms. In short, a flexible principal curve algorithm was used to construct a three-dimensional curve based on the colon images. After the centerline was constructed, a concentration-by-distance curve was estimated along the centerline using the orthogonal projections. The origin of the centerline was normalized to the coccygeal plane defined as the transverse plane crossing the coccyx in the SPECT/CT. The distance between the origin of the centerline and the coccygeal plane was recorded as Dmin (minimum distance associated with the closest point where radiolabeled signal was detected within the luminal path of the colon). Previously defined imaging pharmacokinetic-distance parameters—Dmax (distance associated with the most proximal radiolabel signal within the colon), DCmax (distance at concentration maximum), Dave (mean residence distance)—were calculated for further analysis.

Mucosal Permeability. Four ml blood samples were drawn at 2, 4, 8, 16 and 24 h post dose. Plasma was separated, gamma emissions in 1 ml plasma aliquots were measured on a gamma counter (Wizard2 automatic gamma counter model 2480, PerkinElmer, Waltham, Mass.) within a 110-150-keV energy window, and data corrected for decay relative to the time of dosing. Radioactivity in the plasma was expressed as a fraction of the dose administered to normalize readouts among subjects and products. Area under the concentration-time curve for 24 hours (AUCO-24) and peak concentration (Cmax) were calculated using WinNonlin (Pharsight, 5.1, Cary, N.C.).

Colon Histology. Six formalin-fixed biopsies were embedded, sectioned, stained with hematoxylin-eosin, and assessed by a pathologist blinded to sampling level and enema assignment. Epithelial surface denudation was measured using a categorical scale ranging from 0-3: 0, surface intact; 1—less than ⅓rd surface denuded; 2—⅓rd to ⅔rd surface denuded; 3—more than ⅔rd denudation. Lamina propria hemorrhage was also scored on a scale of 0-3: 0—no hemorrhaging seen; 1—less than ⅓rd of fields with hemorrhaging; 2—between ⅓rd and ⅔rd of fields with hemorrhaging; 3—hemorrhaging detected in more than ⅔rd of the fields examined.

Acceptability. Acceptability of enemas was assessed through a series of web-based questionnaires completed in private settings by the research participants. Questionnaires were conducted (1) prior to receiving any product (Baseline Behavioral Questionnaire [BBQ]), (2) after each inpatient and outpatient product dose (Brief Acceptability Questionnaire [BAQ]), (3) at the end of each product phase (Product Acceptability Questionnaire [PAQ]), and (4) at the end of the study (Overall Product Preference Questionnaire [OPP]). Subjects also participated in a semi-structured interview at the end of the study Data were analyzed using the statistical package STATA/IC 11.2 for Windows software (StataCorp LP, College Station, Tex.). Statistical significance was defined as a p-value <0.05. To analyze the acceptability data, a generalized linear model was used to compare acceptability ratings among the three products controlling for past douching behavior and likelihood of using microbicidal enemas in the future as assessed at the baseline assessment. The normal distribution and identity link was used to analyze continuous variables, whereas the binomial distribution and logit link was chosen to analyze dichotomous outcomes. Generalized estimating equations (GEE) techniques were employed to analyze acceptability data for each outpatient product dose in order to correct for biased estimation of standard errors when correlated within-subject factors are present in time-series data sets. An autoregressive working correlation matrix for all analyses as such selection represented the best model fit according to the Quasi Likelihood under Independence Model Criterion.

The osmolality of solutions is measured using a Wescor Vapro vapor pressure osmometer.

SPECT/CT Evaluation of Distribution and Retention of Enema.

SPECT/CT imaging post-dosing revealed consistent qualitative differences in colon distribution among the enema formulations. Typically, 2-hour post dose fused SPEC/CT images show that the iso-osmolar enema typically distributed through the distal colon and, in some cases, up to the splenic flexure. By contrast, the hyper-osmolar formulation was mostly confined to the rectosigmoid. In fact, no radiolabel was seen 2 hours after the hyper-osmolar enema dose in 3 of 9 subjects. The hypo-osmolar formulation showed a distribution intermediate between the hyper- and iso-osmolar products. The 24-hour post-dose SPEC/CT scans showed retained radiolabel in none of the hyper-osmolar, 3 of the iso-osmolar, and 1 of the hypo-osmolar research participants.

Results

Assessment of quantitative pharmacokinetic-distance parameters showed the iso-osmolar enema had greater (more proximal) Dmax, DCmax, and Dave (Table 1) when compared to the hyper-osmolar enema (mean difference of 21.2, 12.9, and 12.2 cm, respectively, p<0.05) and the hypo-osmolar enema (mean difference of 12.7, 11, and 12.1 cm respectively, p<0.05) adjusting by time from dose (2 or 4 hours). In addition, the iso-osmolar enema had a lower Dmin (more distal location) when compared to the hyper-osmolar enema (mean difference of 1.6 cm, p<0.05) adjusting by time from dose.

TABLE 1

Imaging pharmacokinetic-distance parameters by product at 2 and 4 hours after dosing. Median (25th percentile, 75th percentile).

|  | Iso-osmolar | Hyper-osmolar | Hypo-osmolar |
|---|---|---|---|
| Dmax (cm) | | | |
| 2 hr | 41* (34.7-45.3) | 19.3 (ND-29.9) | 25.5 (18.2-35.1) |
| 4 hr | 38.6* (23.8-41.7) | ND (ND-32.4) | 15.3 (13.8-31.1) |
| DCmax (cm) | | | |
| 2 hr | 22.7* (12.6-29.1) | 6.9 (ND-7.9) | 5.3 (4.4-9.4) |
| 4 hr | 17.5* (8.2-24.1) | ND (ND-7.9) | 6 (2.5-10.5) |
| Dave (cm) | | | |
| 2 hr | 20.6* (17.4-25.6) | 7.7 (ND-7.8) | 8.6 (6.8-11.8) |
| 4 hr | 19.6* (9.8-23.6) | ND (ND-14.4) | 7.9 (5.1-10.3) |
| Dmin (cm) | | | |
| 2 hr | −.001 (−0.3-3.4) | 1.5** (0.6-2) | 1.3 (0.6-1.7) |
| 4 hr | 2 (−1.3-3.4) | 2.9** (1.8-5.1) | 1.7 (0.01-2) |

Dmax: furthest point where radiosignal was detected;
DCmax: distance at concentration maximum;
Dave: mean residence distance;
Dmin: distance associated with the most distal signal;
ND: no signal detected;
*$p < 0.05$, multilevel analysis showed the iso-osmolar enema to have greater Dmax, DCmax, and Dave when compared with the hyper and hypo-osmolar enema adjusting by time from dose;
**$p < 0.05$, multilevel analysis showed the iso-osmolar enema to have lower Dmin when compared with the hyper-osmolar enema adjusting by time from dose.

Histology. Qualitative examination of post-enema biopsy sections revealed that the iso- and hypo-osmolar enema had minimal or no effect on colonic epithelium while the hyper-osmolar enema caused sloughing of the epithelial layer. Quantitative scoring of biopsy sections supported this initial assessment. The epithelial surface denudation caused by iso-osmolar and hypo-osmolar enemas was indistinguishable from baseline (Table 2). However, biopsy sections taken after the hyper-osmolar enema demonstrated significantly greater epithelial sloughing. The odds of having a higher epithelial denudation score in comparison with baseline were 4.2 (95% confidence interval [CI] 1.7-10.1; p<0.05). Regarding lamina propria hemorrhage, the hyper-osmolar enema caused the most damage with an odds of 2.2 (1.04-4.8) compared to baseline (p<0.05) (Table 2) after adjusting for biopsy site, while the iso- and hypo-osmolar treatments had no significant effect (p >0.05).

TABLE 2

Histology, Interferon Gamma induction, tissue and luminal concentrations among products, Geometric Mean Ratios and 95% CI.

| Product | Baseline | Iso-osmolar | Hyper-osmolar | Hypo-osmolar |
|---|---|---|---|---|
| Surface denudation | 1 | 0.5 (0.2-1.5) | 4.2* (1.7-10.1) | 0.6 (0.2-1.7) |
| Lamina propria hemorrhage | 1 | 0.8 (0.3-1.7) | 2.2* (1.04-4.8) | 0.8 (0.4-1.8) |
| Interferon Gamma Concentration | 1 | 0.57* (0.3-0.8) | 0.57* (0.3-0.8) | 0.67 (0.4-1.02) |
| Biopsies | — | 1 | 0.1** (0.07-0.15) | 0.5** (0.3-0.8) |
| Brushes | — | 1 | 0.02** (0.13-0.03) | 0.09** (0.06-0.13) |

*$p < 0.05$ in comparison with baseline, pre-dosing;
**$p < 0.05$ in comparison with iso-osmolar Interferon-Gamma. Colonic mucosa mRNA expression of IFN-γ was decreased one hour after iso-osmolar and hyper-osmolar enemas in comparison with baseline (p<0.05) (Table 2). No change from baseline was seen after the hypo-osmolar distilled water enema.

Tissue and Luminal Concentrations. Concentration of the enema radiolabel in colonic biopsies after hyper- and hypo-osmolar products were lower compared to iso-osmolar enema, 9.4 and 1.8 times, respectively (p<0.01) after adjusting for the distance where colonic biopsies were taken (Table 2). Tissue concentrations at 10 cm were 1.6 times greater (95% CI 1.1-2.4; p<0.05) than at 5 cm and 1.5 times greater (95% CI 1.02-2.3; p<0.05) than at 20 cm after adjusting for enema type.

Similarly, luminal brush concentrations following hyper and hypo-osmolar products were both lower (p<0.01) than with the iso-osmolar enema, 48.5 and 11.1 times, respectively (p<0.01), adjusting for the distance where samples were taken. Luminal brush concentrations at 10 and 20 cm were 3.4 (95% CI 2.3-5.1; p<0.01) and 2.1 (95% CI 1.4-3.1; p<0.01) times greater, respectively, than at 5 cm after adjusting for enema type.

Permeability. The hypo-osmolar enema had a greater plasma 99mTc-DTPA AUCO-24 when compared to the hyper-osmolar enema and a greater Cmax when compared to the iso-osmolar enemas (Table 3; both p<0.05). In addition, the iso-osmolar enema had a greater Tmax when compared with hyper- and hypo-osmolar enema.

TABLE 3

Permeability parameters by product. Median (25th percentile, 75th percentile).

|  | Iso-osmolar | Hyper-osmolar | Hypo-osmolar |
|---|---|---|---|
| AUC0-24 (×107 μCi hr/ml) | 19.7 (8.4-27.4) | 9.4 (8.7-13) | 21.4* (17.4-44.9) |
| Cmax (×107 μCi/ml) | 1.7 (0.7-2.5) | 2.1 (1.5-2.8) | 3.5** (2.8-8) |
| Tmax (hr) | 3.7*** (2.6-4) | 2 (1.7-3) | 2 (1.7-3) |

*$p < 0.05$, multilevel analysis showed the hypo-osmolar enema to have greater AUC when compared to the hyper-osmolar enema;
**$p < 0.05$, multilevel analysis showed the hypo-osmolar enema to have greater Cmax when compared to the iso-osmolar enema;
***$p < 0.05$, multilevel analysis showed the iso-osmolar enema to have a greater Tmax when compared to the hyper-and hypo-osmolar enema.

Acceptability of Enema Products. According to data from the baseline assessment, all nine participants had used enemas in preparation for sex, ranging from 2 to 24 times in the prior 6 months, six of whom reported using enemas always or frequently before sex. Only two participants used enemas following sex. At baseline, 5 of 9 subjects (56%) indicated they were extremely likely to use a microbicidal enema in the future. In the BAQ administered after every enema dose, 7 of 9 participants indicated no change or increase in sexual satisfaction. A different subject for each product identified each of the 3 products as unacceptable. After all doses of a product had been used, when participants were asked to indicate overall, how much they liked the product in the PAQ using a Likert scale (10, "liked very much"), the three enemas were rated similarly: mean (SD) hyper-osmolar 7.8 (2.4), iso-osmolar 7.6 (2.6), hypo-osmolar 7.7 (2.8) with all 3 products having a range in scores from 2-10.

A several day long half-life of intracellular TFV-DP showed that TFV is the candidate most likely to sustain one week of protective concentrations and also avoid high concentration peaks that occur with shorter half-life drugs.

Topical TDF has advantages over oral dosing. TDF does not reach iPrEx EC90 PBMC concentrations until 7 days of 300 mg TDF doses; double dosing (600 mg TDF daily) shortens time to protection to 3 days.

Colon CD4+ cells are HIV mucosal targets and relevant for estimating protective TFV concentrations for development of the microbicidal compositions. Colorectal tissue, including the activated CD4+ T cells, are definable, early targets for HIV infection during URAI, and are able to be acquired safely via endoscopic biopsies. TFV-DP concentrations in isolated mucosal CD4+ T cells are better predictors of ex vivo tissue infectibility by HIV (explant assays) than rectal fluid or whole biopsy homogenates. Colon tissue CD4+ cells are also better predictors of ex vivo HIV explant challenge results compared to plasma or rectal fluid TFV and colon tissue homogenate TFV-DP concentrations.

SUMMARY

Mildly hypotonic fluid significantly enhances the amount and rate of drug uptake into colon tissue, supporting prolonged drug delivery. Hypotonic formulations cause very rapid absorption of fluid via an osmotic gradient and by actively pumping sodium out of the lumen. This fluid uptake causes advective drug transport into the epithelium.

EXAMPLE 3

Dose Escalation

Based on the more conservative "dose-based" gel-equivalent enema dose estimate described above, three sequential doses in each of 18 healthy male research participants are proposed:

The following formulations were prepared for the studies in the examples. Hypotonic formulations were prepared with and without gel.

Product A: Isotonic Initial Enema Dose

Product A will contain TFV 220 mg in 125 mL normal saline with sufficient sodium hydroxide to maintain physiological pH. This dose is selected to achieve the same colon tissue CD4+ cell TFV-DP concentration as a TFV 1% rectal gel dose. This will provide data to compare TFV 1% gel to an enema formulation.

Product B: Isotonic Escalation Enema Dose

Product B will contain TFV 660 mg in 125 mL normal saline with sufficient sodium hydroxide to maintain physiological pH. This is three times the total dose and concentration as planned for Product A. This dose is estimated to achieve colon tissue CD4+ cell concentrations below the concentrations achieved with 5 days of TFV 1% rectal gel dosing in RMP-02/MTN-006. This will provide data on tissue TFV dose proportionality with Product A.

Product C: Hypotonic Escalation Enema Dose

Product C will contain TFV 660 mg in 125 mL normal saline with sufficient sodium hydroxide to maintain physiological pH, at half the NaCl concentration of normal saline. This is selected to be the same dose as Product B, but with approximately one-half the tonicity. This will provide data on increased tissue TFV-DP concentration with a hypotonic enema when compared to an isotonic enema formulation.

Product A is anticipated to achieve tissue concentrations of TFV-DP at least 3-fold lower than concentrations achieved with 7 days of 1% TFV gel dosing (based on RMP-01/MTN-006).

Product B. The precise dose of escalation iso-osmolar dose (Product B) will be based on the results of the initial iso-osmolar Product A colon tissue concentrations and safety assessment in the first 6 research participants with the goal of achieving colon tissue homogenate and CD4+ cell TFV-DP concentrations equivalent to 3 times the single TFV 1% gel dose which is estimated to be bracketed by the iPrEx-based IC90 colon tissue targets. This 3× iso-osmolar escalation dose is roughly similar to concentrations achieved with 5 days of TFV 1% gel dosing. Escalation iso-osmolar Product C will be adjusted as follows based on relationship to the initial dose "target" median colon tissue TFV-DP homogenate and CD4+ cell concentrations:

If the initial TFV enema dose is within +50% of the concentration target, then the escalation dose will be 660 mg.

If the initial TFV enema dose is less than 50% of the median concentration target, then the escalation dose will be increased to achieve 3-times the initial dose target based on the ratio of the initial enema dose and the TFV 1% gel colon tissue TFV-DP concentrations.

If the initial TFV enema dose is greater than 50% of the median concentration target, then the escalation dose will be decreased to achieve 3-times the initial dose target based on the ratio of the initial enema dose and the TFV 1% gel colon tissue TFV-DP concentrations. If this estimate is less than twice the initial dose, then the escalation dose will be skipped and research participants will advance to the hypotonic enema dose at the same dose as the initial dose.

Product C. The escalation hypotonic enema, Product C, will be 150 mOsm to enhance TFV tissue uptake, and this approach is consistent with prior findings in both animal models and clinical studies. The dose will not be adjusted based on Dose 2 results in order to allow a straightforward evaluation of the effect of tonicity on tissue penetration without assumptions about linear resealing that a dose-adjustment might necessitate. It is estimated that the hypotonic enema to achieve tissue concentrations up to 2 times that achieved with an equivalent isotonic dose. The tonicity is half-way between iso-osmolar and zero tonicity in an attempt to maintain the luminal distribution advantages seen with prior iso-osmolar enemas compared to tap water enemas.

Beyond the rules for dose escalation adjustments, the following overall two-tiered safety ceilings are established based on drug concentrations assessed in the first 6 research participants in each dose level are also set for this study:

Below the systemic (blood) TFV concentrations associated with peak (Cmax) concentrations after a single oral TDF dose of 350 ng/mL.

Below 4 times the upper bound of the colon CD4+ cell TFV-DP concentration peak (2,000 fmol/106 cell Cmax) that are predicted to provide 90% protection at 7 days (85 fmol/106 cells).

If these limits are exceeded, the dose will be adjusted to stay below these limits. In addition, the escalation from the higher of two doses to the hypotonic formulation (Product 2→Product 3) may need to be adjusted downward if the hypotonic enema enhancement demonstrated in NHP studies indicate the two-tier safety concentration ceilings will be exceeded. Escalation Guidelines. Three criteria will need to be met for escalation to the next dose cohort:

(1) PK target criteria (described above)

(2) PK safety criteria (described above)

(3) Clinical safety criteria (described in clinical protocol)

EXAMPLE 4

Condom Integrity

Materials and Methods

The compatibility of original TFV 1% gel (VF) was tested with three types of lubricated male latex condoms. A matched placebo gel and Universal HEC Placebo Gel were used as comparator gels. The condoms tested were representatives of leading brands on the US market (Trojan® and Durex®) with either silicone or aqueous lubricant. The airburst test was used to evaluate changes in film integrity (strength) and test specimens were measured before and after treatment with the gels to assess changes in strength properties following the application of the three gel preparations.

Results

All three gels (the original vaginal gel, matched placebo, and Universal HEC Placebo gel) were shown to be compatible with the above condoms.

The RF was shown to be compatible with lubricated and non-lubricated latex condoms using the Magee condom compatibility test based on the Texture Analyzer. A second condom compatibility study with the RF was performed by FHI using the ASTM standard testing protocol (ASTM D7661-10). In this testing, 6 styles of condoms were evaluated: 3 non-lubricated latex (Durex®, Lifestyles®, and Trojan®), 2 polyisoprene (Avanti Bare® and Lifestyles SKYN®), and 1 polyurethane (Trojan Supra®). The condoms were treated with the RF gel and tested for tensile (break force and elongation) and airburst (pressure and volume) properties. Untreated condoms subjected to testing procedures served as a control; condoms treated with a known degradant served as a positive control.

The condom testing data for the RF gel was evaluated for statistical significance using Tukey's multiple range test. Overall, in 20 of the 24 sets of results (4 tests and 6 condoms) there were either no significant differences between the treated and control groups or the treated group performed significantly better than the control. In the four sets of results in which the treated condoms performed significantly worse than the controls, which were observed for two of the non-lubricated latex condoms and for the polyurethane condom, the differences were much smaller (at least 74% smaller) than those observed after condom exposure to the known degradant. There were no significant differences between the treated and control groups for the polyisoprene condoms.

We claim:

1. A hypotonic microbicidal composition comprising an effective amount of a microbiocide as a free drug to inhibit infection or replication, and a pharmaceutically acceptable carrier suitable for administration rectally or vaginally, wherein the composition has an effective osmolarity between 20 and 290 mOsm for tissue uptake at the rectal or vaginal site for a period of at least about 1 hour up to seven days following administration.

2. The composition of claim 1 wherein the microbiocide is an antiviral.

3. The composition of claim 2, wherein the antiviral is a nucleoside reverse transcription inhibitor (NRTI) selected from the group consisting of tenofovir, tenofovir alafenamide fumarate, tenofovir disoproxil fumarate, and hexadecyloxypropyl tenofovir.

4. The composition of claim 1 having an osmolarity between 50 and 280 mOsm.

5. The composition of claim 1 having an osmolarity between 100 and 200 mOsm.

6. The composition of claim 1 comprising sodium.

7. The composition of claim 6 further comprising potassium.

8. The composition of claim 1 in a container for administration as an enema.

9. The composition of claim 8 wherein the container contains a solution or a dry formulation which is hydrated at the time of use.

10. A method for administration of a microbiocide comprising administering to the subject rectally an effective amount of the microbicidal composition of claim 1.

11. The method of claim 10 wherein the microbiocide composition is administered prior to or post receptive anal intercourse (RAI).

12. The method of claim 10, wherein the microbiocidal composition is administered in one dose.

13. The method of claim 10 wherein the microbiocidal is administered to produce an effective amount in the colon for a period of more than a day.

14. The composition of claim 6, wherein the composition comprises 25 mM sodium.

15. The method of claim 13, wherein the microbiocidal is administered to produce an effective amount in the colon for a period of seven days.

16. The method of claim 10, wherein the microbiocidal composition is in a container in a solution or in a dry form, which is hydrated at the time of use, for administration as an enema.

* * * * *